United States Patent [19]
Berg

[11] Patent Number: 5,466,345
[45] Date of Patent: Nov. 14, 1995

[54] SEPARATION OF O-XYLENE FROM P-XYLENE AND M-XYLENE BY AZEOTROPIC DISTILLATION

[75] Inventor: Lloyd Berg, 1314 S. Third Ave., Bozeman, Mont. 59715

[73] Assignee: Lloyd Berg, Bozeman, Mont.

[21] Appl. No.: 454,624

[22] Filed: May 31, 1995

[51] Int. Cl.$^6$ .................. B01D 3/36; C07C 7/06
[52] U.S. Cl. .................. 203/57; 203/58; 203/60; 203/62; 203/63; 203/66; 203/67; 585/805; 585/860; 585/864; 585/865; 585/866
[58] Field of Search .................. 203/66, 63, 60, 203/62, 58, 67, 57; 585/805, 808, 860, 864, 865, 866

[56] References Cited

U.S. PATENT DOCUMENTS

| | | | |
|---|---|---|---|
| 2,456,561 | 12/1948 | Lake et al. | 203/60 |
| 2,763,604 | 9/1956 | Dorsey et al. | 203/60 |
| 3,227,632 | 1/1966 | Schmdlenbach et al. | 203/58 |
| 4,488,937 | 12/1984 | Berg et al. | 203/60 |
| 4,673,465 | 6/1987 | Berg et al. | 203/57 |
| 5,039,380 | 8/1991 | Berg | 203/60 |
| 5,094,723 | 3/1992 | Berg | 203/60 |
| 5,094,725 | 3/1992 | Berg | 203/60 |

Primary Examiner—Wilbur Bascomb, Jr.

[57] ABSTRACT o-Xylene cannot be separated from p-xylene and m-xylene by conventional distillation or rectification because of the proximity of their boiling points. o-Xylene can be readily separated from mixtures of p-xylene and m-xylene by azeotropic distillation. Effective agents are 3-methyl-1-butanol, methyl propionate and 3-pentanone.

1 Claim, No Drawings

5,466,345

SEPARATION OF O-XYLENE FROM P-XYLENE AND M-XYLENE BY AZEOTROPIC DISTILLATION

FIELD OF THE INVENTION

This invention relates to a method for separating o-xylene from a mixture with p-xylene and m-xylene using certain organic liquids as the agent in azeotropic distillation.

DESCRIPTION OF PRIOR ART

Azeotropic distillation is the method of separating close boiling compounds or azeotropes from each other by carrying out the distillation in a multiplate rectification column in the presence of an added liquid, said liquid forming an azeotrope with one or both of the compounds to be separated. Its presence on each plate of the rectification column alters the relative volatility in a direction to make the separation on each plate greater and thus require either fewer plates to effect the same separation or make possible a greater degree of separation with the same number of plates. The azeotrope forming agent is introduced with the feed to a continuous column. The azeotrope forming agent and the more volatile component are taken off as overhead product and the less volatile component comes off as bottoms product. The usual methods of separating the azeotrope former from the more volatile component are cooling and phase separation or solvent extraction.

The usual method of evaluating the effectiveness of azeotropic distillation agents is the change in relative volatility of the compounds to be separated. Table 1 shows the degree of separation or purity obtainable by theoretical plates at several relative volatilities. Table 1 shows that a relative volatility of at least 1.2 is required to get an effective separation by rectification.

TABLE 1

Effect of Relative Volatility on Theoretical Stage Requirements.

| Separation Purity, Both Products (Mole Fraction) | Relative Volatility | | | | | | | |
|---|---|---|---|---|---|---|---|---|
| | 1.02 | 1.1 | 1.2 | 1.3 | 1.4 | 1.5 | 2.0 | 3.0 |
| | Theoretical Stages at Total Reflux | | | | | | | |
| 0.999 | 697 | 144 | 75 | 52 | 40 | 33 | 19 | 12 |
| 0.995 | 534 | 110 | 57 | 39 | 30 | 25 | 14 | 9 |
| 0.990 | 463 | 95 | 49 | 34 | 26 | 22 | 12 | 7 |
| 0.98 | 392 | 81 | 42 | 29 | 22 | 18 | 10 | 6 |
| 0.95 | 296 | 61 | 31 | 21 | 16 | 14 | 8 | 4 |
| 0.90 | 221 | 45 | 23 | 16 | 12 | 10 | 5 | 3 | p-Xylene boils at 138.4° C., m-xylene at 139.1° C. and m-xylene at 144.5° C. The relative volatility of p-xylene from m-xylene is 1.02; for m-xylene from o-xylene it is 1.12 and are virtually impossible to separate by conventional distillation or rectification. Azeotropic distillation would be an attractive method of effecting the separation of o-xylene from p-xylene and m-xylene if agents can be found that (1) will enhance the relative volatility between o-xylene and p-xylene and m-xylene and (2) is easy to recover from the xylenes. The advantage of using azeotropic distillation in this separation can be seen from the data shown in Table 1. If an agent can be found that will increase the relative volatility to 1.4, 99% purity of m-xylene from o-xylene can be obtained with only 26 plates.

OBJECTIVE OF THE INVENTION

The object of this invention is to provide a process or method of azeotropic distillation that will enhance the relative volatility of o-xylene from p-xylene and m-xylene in their separation in a rectification column. It is a further object of this invention to identify organic compound azeotropic distillation agents that are stable and can be separated from xylenes.

SUMMARY OF THE INVENTION

The objects of this invention are provided by a process for the separation of o-xylene from p-xylene and m-xylene which entails the use of certain organic compounds which will enhance the relative volatility of o-xylene from p-xylene and m-xylene when used as the agent in azeotropic distillation.

DETAILED DESCRIPTION OF THE INVENTION

I have discovered that certain organic compounds will increase the relative volatility of o-xylene from p-xylene and m-xylene when used as the agent in azeotropic distillation. The effective agents are methanol, ethanol, isopropanol, cyclopentanol, 1-butanol, n-amyl alcohol, 3-methyl-1-butanol, methyl acetate, methyl trimethyl acetate, propyl formate, methyl propionate, methyl pivalate, butyl formate, methyl lactate, n-pentyl propionate, butyl benzoate, methyl butyrate, isobutyl acetate, acetal, dimethyl carbonate, diethyl carbonate, propyl propionate, 2,3-butanedione, chloroform, methylene chloride, trichloroethylene, 1,1,2-trichloroethane, tetrahydrofuran, t-butyl methyl ether, t-amyl methyl ether, isopropyl ether, benzyl cyanide, butyraldehyde oxime, 2-butanone, 3-pentanone, butyraldehyde, 1,1,1-trichloroethane and 1-methyl piperazine.

WORKING EXAMPLES

Example 1

Fifteen grams of m-xylene, 9 grams of p-xylene and 6 grams of o-xylene and 30 grams of methyl propionate were charged to a vapor-liquid equilibrium still and refluxed for 5 hours. Analysis indicated a vapor composition of 32.1% p-xylene, 52.6% m-xylene and 15.3% o-xylene; a liquid composition of 29.8% p-xylene, 49.8% m-xylene and 20.4% o-xylene. This is a relative volatility of m-xylene to o-xylene of 1.4 and of p-xylene to o-xylene of 1.44.

TABLE 3

Effective Azeotropic Distillation Agents For Separating o-Xylene From p-Xylene And m-Xylene

| Compounds | Relative Volatility |
|---|---|
| None | 1.1 |
| Methanol | 1.35 |
| Ethanol | 1.3 |
| Isopropanol | 1.35 |
| Cyclopentanol | 1.3 |
| 1-Butanol | 1.4 |

TABLE 3-continued

Effective Azeotropic Distillation Agents For
Separating o-Xylene From p-Xylene And m-Xylene

| Compounds | Relative Volatility |
|---|---|
| n-Amyl alcohol | 1.3 |
| 3-Methyl-1-butanol | 1.4 |
| Methyl acetate | 1.4 |
| Methyl trimethyl acetate | 1.35 |
| Propyl formate | 1.4 |
| Methyl propionate | 1.4 |
| Methyl pivalate | 1.3 |
| Butyl formate | 1.3 |
| Methyl lactate | 1.3 |
| n-Pentyl propionate | 1.3 |
| Butyl benzoate | 1.3 |
| Methyl butyrate | 1.3 |
| Isobutyl acetate | 1.3 |
| Acetal | 1.35 |
| Dimethyl carbonate | 1.3 |
| Diethyl carbonate | 1.3 |
| Propyl propionate | 1.3 |
| 2,3-Butanedione | 1.3 |
| Chloroform | 1.35 |
| Methylene chloride | 1.35 |
| Trichloroethylene | 1.3 |
| 1,1,2-Trichloroethane | 1.3 |
| Tetrahydrofuran | 1.35 |
| t-Butyl methyl ether | 1.35 |
| t-Amyl methyl ether | 1.35 |
| Isopropyl ether | 1.35 |
| Butyraldehyde oxime | 1.3 |
| Benzyl cyanide | 1.35 |
| 2-Butanone | 1.3 |
| 3-Pentanone | 1.33* |
| Butyraldehyde | 1.35 |
| 1,1,1-Trichloroethane | 1.35 |
| 1-Methyl piperazine | 1.3 |

*Data obtained in multiplate column

Example 2

100 grams of p-xylene, 30 grams of m-xylene, 20 grams of o-xylene and 100 grams of 3-pentanone were placed in the stillpot of a 5.6 theoretical plate glass perforated plate rectification column and operated at total reflux for four hours. Analysis indicated a vapor composition of 68.2% p-xylene, 22.6% m-xylene and 9.2% o-xylene; a liquid composition of 52.4% p-xylene, 16.0% m-xylene and 31.6% o-xylene. This is a relative volatility of m-xylene to o-xylene of 1.33 and of p-xylene to o-xylene of 1.3.

I claim:

1. A method for recovering o-xylene from a mixture of o-xylene, p-xylene and m-xylene which comprises distilling a mixture of o-xylene, p-xylene and m-xylene in the presence of an azeotrope forming agent, recovering the p-xylene, the m-xylene and the azeotrope forming agent as overhead product and obtaining the o-xylene as bottoms product, wherein said azeotrope forming agent consists of one material selected from the group consisting of methanol, ethanol, isopropanol, cyclopentanol, 1-butanol, n-amyl alcohol, 3-methyl-1-butanol, methyl acetate, methyl trimethyl acetate, propyl formate, methyl propionate, methyl pivalate, butyl formate, methyl lactate, n-pentyl propionate, butyl benzoate, methyl butyrate, isobutyl acetate, acetal, dimethyl carbonate, diethyl carbonate, propyl propionate, 2,3-butanedione, chloroform, methylene chloride, trichloroethylene, 1,1,2-trichloroethane, tetrahydrofuran, t-butyl methyl ether, t-amyl methyl ether, isopropyl ether, butyraldehyde oxime, benzyl cyanide, 2-butanone, 3-pentanone, 1,1,1-trichloroethane, butyraldehyde and 1-methyl piperazine.

* * * * *